US006372752B1

(12) United States Patent
Staveski et al.

(10) Patent No.: US 6,372,752 B1
(45) Date of Patent: Apr. 16, 2002

(54) INHA INHIBITORS AND METHODS OF USE THEREOF

(75) Inventors: Mark M. Staveski, Taunton; Scott F. Sneddon, Salem; Christopher Yee, Needham; Andrew Janjigian, Cambridge, all of MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/499,183

(22) Filed: Feb. 7, 2000

(51) Int. Cl.$^7$ ..................... A61K 31/505; C07D 401/04

(52) U.S. Cl. ....................... 514/273; 514/249; 514/256; 544/331; 544/333; 544/353

(58) Field of Search ................................ 514/249, 256, 514/273; 544/331, 333, 353

(56) References Cited

U.S. PATENT DOCUMENTS 4,772,608 A * 9/1988 Sasse et al. ................. 514/275
5,134,142 A * 7/1992 Matsuo et al. .............. 514/255

FOREIGN PATENT DOCUMENTS

EP 515041 A2 * 11/1992

OTHER PUBLICATIONS

"Results from Library Synthesis and Screening: a Biotech. Case Study," published in the book of Abstracts from the Conference Exploiting Moloecular Diversity in San Diego, CA, Feb. 1–3, 1999.

* cited by examiner

*Primary Examiner*—Ceila Chang
(74) *Attorney, Agent, or Firm*—Hamilton, Brook, Smith & Reynolds, P.C.

(57) ABSTRACT

The invention relates to compounds which inhibit the Mycobacterial enoyl-ACP reductase required for cell wall biosynthesis. The invention also relates to pharmaceutical compositions comprising these compounds and to methods of use of these compounds for treating a bacterial infection in a patient.

20 Claims, No Drawings

INHA INHIBITORS AND METHODS OF USE THEREOF

BACKGROUND OF THE INVENTION

Tuberculosis is the leading cause of death from infectious disease in the world. Virtually all cases of this disease in humans are caused by the bacterium =Mycobacterium tuberculosis. The disease is often limited to the lungs but can involve extrapulmonary sites, such as the lymph nodes, pleura, genitourinary tract, bones and joints, peritoneum and the meninges. Pulmonary tuberculosis is characterized by a persistent cough, fever and weight loss.

Tuberculosis accounted for 20% to 30% of all deaths in urban, industrialized societies during the eighteenth and nineteenth centuries. In the past century, deaths attributable to tuberculosis in the United States and other industrialized countries have declined dramatically, due in part to public health measures, such as improved sanitation and early detection programs, and the use of antibiotics. However, tuberculosis remains a significant source of mortality in developing countries, and it is estimated that half of the world's population is infected with *M. tuberculosis*, while 30 million people have the active disease. In addition, the incidence of tuberculosis in the United States has increased since 1985. This increase has been attributed to several factors, including immigration, an increase in the number of people who are homeless or living in substandard housing, an increase in the number of immune-compromised people, such as AIDS patients, and the emergence of drug-resistant strains of *M.tuberculosis.*

Although the mechanism by which *M. tuberculosis* causes disease is not established, the organism has proven susceptible to a variety of antimicrobial drugs. The primary drugs used to treat active tuberculosis include isoniazid, ethambutol, rifampin, pyrazinamide and streptomycin. Prophylactic therapy, generally involving administration of isoniazid alone, is also employed when *M. tuberculosis* infection is known or suspected but active disease is not yet present. Current treatment regimens for active tuberculosis generally involve continuous treatment with two or more antibiotics, in an effort to prevent the development of resistant strains. While such treatment usually renders the patient non-infectious within one or two weeks, it must be continued for several months to rid the patient of infection. The duration of the treatment period and the need for multiple daily dosings of two or more drugs lead to a lack of patient compliance, which in turn contributes to the development of drug resistant strains. The emergence of drug resistant strains is rendered still more problematic as, except for isoniazid, the molecular targets of the commonly used antibiotics are unknown.

The mortality and morbidity associated with tuberculosis worldwide, the increasing incidence of this disease in industrialized countries and the decreasing effectiveness of current therapies all point to the need for new approaches and chemotherapeutic agents for the treatment and prophylaxis of this disease.

SUMMARY OF THE INVENTION

The present invention provides compounds that are useful for the treatment of bacterial infections, pharmaceutical compositions comprising these compounds and methods of use of these compounds and/or pharmaceutical compositions for the treatment or prophylaxis of bacterial infection.

In one embodiment, the invention provides compounds of Formula I, (I)

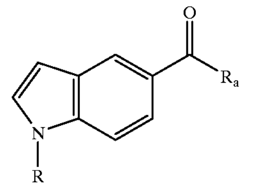

wherein $R_a$ is a substituted or unsubstituted heterocyclic group and R is hydrogen, alkyl, aryl, heteroaryl, arylalkyl or heteroarylalkyl.

In another embodiment, the invention provides compounds of Formula II, (II)

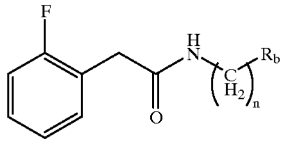

where n is 1 or 2 and $R_b$ is hydroxy, cycloalkenyl, substituted or unsubstituted phenyl, indolyl or diphenylmethyl.

In a further embodiment, the invention relates to compounds of Formula III, (III)

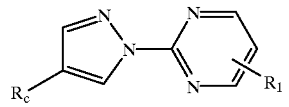

where $R_c$ is a substituted or unsubstituted aryl or heteroaryl group and $R_1$ represents one or more substituents independently selected from hydrogen, halogen, trifluoromethyl, alkyl, alkoxy, nitro and cyano.

The invention also relates to compounds of Formula IV, (IV)

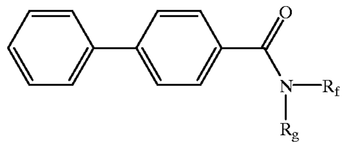

where $R_f$ and $R_g$ are each, independently, substituted or unsubstituted alkyl, substituted or unsubstituted arylalkyl or substituted or unsubstituted heteroarylalkyl.

In another aspect, the invention relates to compounds of Formula V, (V)

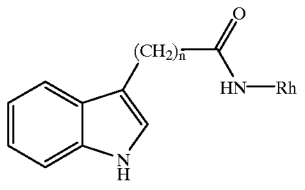

where n is 1, 2 or 3 and $R_h$ is substituted or unsubstituted aryl, arylalkyl, alkenyl or cycloalkyl In another embodiment, the invention provides pharmaceutical compositions comprising one or more compounds of Formulas I, II, III, IV or V. These compositions can, for example, comprise a therapeutically effective amount of a compound or compounds of Formulas I, II, III, IV or V and one or more pharmaceutically acceptable carriers, diluents or excipients, or a combination thereof.

In yet another embodiment, the invention relates to a method of treating a bacterial infection in a patient. The method comprises administering to the patient a therapeutically effective amount of one or more compounds of Formulas I, II, III, IV or V. The bacterial infection can be an infection by any bacterial species, such as a pathogenic bacterial species, and is preferably an infection by a pathogenic Mycobacterium species or a Gram-negative bacterial species.

DETAILED DESCRIPTION OF THE INVENTION

The enoyl-ACP reductase (referred to herein as "InhA") encoded by the Mycobacterium gene inhA is an essential enzyme in the biosynthesis of mycolic acid, the single most abundant component of the *Mycobacterium tuberculosis* cell wall. Thus, this enzyme is required by this organism for cell wall synthesis, and inhibition of this enzyme results in death of the bacterial cell. At least one of the antibiotics commonly used for treatment or prophylaxis of tuberculosis, isoniazid, results in inhibition of InhA. Isoniazid, however, is not a direct inhibitor of InhA, and must be converted to an active metabolite by the catalase-peroxidase encoded by the bacterial gene katG. This requirement for initial metabolism of isoniazid has provided *M. tuberculosis* with a mechanism for developing drug resistance. For example, certain isoniazid-resistant strains of *M. tuberculosis* have a mutant katG gene and consequently do not produce the active catalase-peroxidase. Other bacteria, such as Gram negative bacteria, have been shown to have a gene which is believed to encode an enoyl-ACP reductase similar to that of the Mycobacteria, and this enzyme is an appropriate drug target in the treatment of infections by these organisms as well.

The present invention relates to the discovery of compounds which are direct inhibitors of InhA; that is, these compounds are capable of inhibiting InhA without first undergoing metabolic conversion. These compounds, therefore, offer a significant advantage in treating bacterial infections compared to drugs in current use, such as isoniazid, because they eliminate at least one possible pathway for the development of drug resistance.

For the purposes of the present invention, the term "alkyl" refers to a straight chain or branched saturated hydrocarbyl group. Preferred alkyl groups include $C_1$–$C_{12}$-alkyl groups, while more preferred alkyl groups include $C_1$–$C_6$-alkyl groups. The term "cycloalkyl" refers to a mono-, bi- or polycyclic alkyl group. Preferred cycloalkyl groups include $C_3$–$C_8$-cycloalkyl groups. The term "alkoxy" refers to an alkyl-O- group or a cycloalkyl-O- group, where the preferred alkyl and cycloalkyl groups are those given above. The term "alkenyl" refers to a straight chain or branched hydrocarbyl group which includes one or more double bonds. Preferred alkenyl groups include $C_2$–$C_{12}$-alkenyl groups. The term "cycloalkenyl" refers to a cyclic hydrocarbyl group which includes one or more double bonds but is not aromatic. Preferred cycloalkenyl groups include $C_5$–$C_8$-cycloalkenyl groups.

The term "aryl" refers to an aromatic carbocyclic group, such as a phenyl group, a naphthyl group or a phenyl or naphthyl group which is fused with a a five or six-membered carbocyclic or heterocyclic ring.

The terms "heterocycle" and "heterocyclic group" refer to a saturated, aromatic or partially unsaturated ring system which includes at least one heteroatom, such as one or more oxygen, nitrogen or sulfur atoms or a combination thereof. Saturated heterocyclic groups ("heterocycloalkyl groups") include piperidyl, pyrollidyl, piperazyl tetrahydrofuranyl and morpholyl.

The term "heteroaryl" refers to an aromatic heterocyclic group. Suitable heteroaryl groups include, but are not limited to, pyridyl, pyrimidyl, quinolyl, isoquinolyl, pyrrolyl, quinoxalyl, imidazolyl, oxazolyl, isoxazolyl, pyrazolyl, thienyl, furanyl, pyrazolyl, thiadiazolyl, oxadiazolyl, indazolyl, thiazolyl, isothiazolyl, and tetrazolyl. Heteroaryl groups also include ring systems in which a carbocyclic aromatic ring, carbocyclic non-aromatic ring or heteroaryl ring is fused to one or more other heteroaryl rings (e.g., benzo(b)thienyl, benzimidazolyl, benzoxazolyl, benzothiazolyl, benzothiadiazolyl, benzoxadiazolyl, indolyl, tetrahydroindolyl, azaindolyl, indazolyl, quinolinyl, imidazopyridyl, puryl, pyrrolo[2,3-d]pyrimidyl, pyrazolo[3,4-d]pyrimidyl).

The term "arylalkyl" refers to an alkyl group which is substituted by one or more substituted or unsubstituted aryl groups. Preferred arylalkyl groups include benzyl, diphenylmethyl and 2-phenethyl groups. The term "heteroarylalkyl" refers to an alkyl group which is substituted by a substituted or unsubstituted heteroaryl group.

Alkyl, cycloalkyl, alkenyl, cycloalkenyl and alkoxy groups can be substituted or unsubstituted. Substituted groups of this type can include, for example, one or more substituents such as halo, including fluoro, chloro, bromo and iodo; alkyl, such as $C_1$–$C_6$-alkyl; nitro; cyano; aryl groups, cycloalkyl groups and heterocyclic groups.

Aryl and heterocyclic, such as heteroaryl, groups can be substituted or unsubstituted. Suitable substituents include one or more substituents independently selected from halo, such as fluoro, chloro, bromo or iodo; alkyl, preferably $C_1$–$C_3$-alkyl; alkoxy, preferably $C_1$–$C_3$-alkoxy; nitro; methylenedioxo; aryl groups and heterocyclic groups.

In one embodiment, the invention relates to compounds of Formula I, (I)

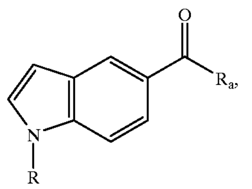

where $R_a$ is a substituted or unsubstituted heterocyclic group and R is hydrogen or a substituted or unsubstituted alkyl, cycloalkyl, cycloalkylalkyl, arylalkyl or heterocyclyl-alkyl group. For example, $R_a$ can be a heterocycloalkyl group, a heteroaryl group or partially unsaturated heterocyclic group, such as heterocycloalkene or heterocycloalkadiene group. Preferably, $R_a$ is a 5-, 6- or 7-membered heterocyclic group which can, optionally, be fused to a 5- or 6-membered heterocyclic or carbocyclic ring. R is, preferably, a $C_1$–$C_6$ alkyl group, a phenyl-$C_1$–$C_6$-alkyl group, a $C_3$–$C_8$-cycloalkyl-$C_1$–$C_6$-alkyl group or a heterocyclyl-$C_1$–$C_6$-alkyl group, such as a 1-piperidinyl-$C_1$–$C_6$-alkyl group.

Suitable substituents on the heterocyclic group include halogen atoms, hydroxyl, nitro, trifluoromethylcarbonylamino, alkoxycarbonyl, cyano, alkylcarbonylamino, amino, alkylamino, dialkylamino, $C_1$–$C_4$-alkyl, $C_1$–$C_4$-alkoxy, aryl, arylalkyl, substituted and unsubstituted fluorenyl, arylcarbonyl and alkylcarbonyl groups. The foregoing groups can be substituted or unsubstituted. Preferred substituents on these groups include $C_1$–$C_6$-alkyl groups and halogen atoms.

In one embodiment, $R_a$ is substituted or unsubstituted isoquinolyl, quinolyl, tetrahydroisoquinolyl, piperidyl or morpholyl. For example, $R_a$ can be 4,5-dimethoxy-1,2,7,8-tetrahydro-1-isoquinolyl, 1,2,7,8-tetrahydro-1-isoquinolyl, 2-quinolyl, 3,5-dimethyl-1-morpholyl, 4-butanoyl-4-phenyl-1-piperidyl, 4-benzoyl-1-piperidyl or substituted 4-benzoyl-1-piperidyl, for example 4-(halo-substituted-benzoyl)-1-piperidyl, such as 4-(4-fluorobenzoyl)-1-piperidyl, 4-(4-chlorophenyl)- 1 -piperidyl or 4-(pentamethylbenzoyl)- 1 -piperidyl.

In another embodiment, $R_a$ is a 1-piperazinyl group of the formula

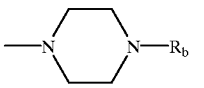

where $R_b$ is a substituted or unsubstituted aryl, arylalkyl heteroaryl or fluorenyl group. Preferably, $R_b$ is substituted or unsubstituted benzyl, substituted or unsubstituted diphenylmethyl, substituted or unsubstituted phenyl, substituted or unsubstituted fluorenyl, substituted or unsubstituted pyridyl or substituted or unsubstituted furfuryl. Preferred substituents on the group $R_b$ include one or more halogen atoms, hydroxyl, nitro, trifluoromethylcarbonylamino, alkoxycarbonyl, cyano, alkylcarbonylamino, amino, alkylamino, dialkylamino, $C_1$–$C_4$-alkyl, $C_1$–$C_4$-alkoxy, aryl, arylalkyl, arylcarbonyl, alkylcarbonyl or trifluoromethyl groups. In one embodiment, $R_b$ is selected from the group consisting of benzyl, diphenylmethyl, phenyl, 2-methoxyphenyl, 2-pyridyl, 3,4-methylenedioxybenzyl, 4-fluorophenyl, 4-chlorophenyl, 3-chloro-6-methylphenyl, 3-trifluoromethylphenyl and fluorenyl substituted with one or more nitro groups or halogen atoms.

In another embodiment, $R_b$ is of the formula

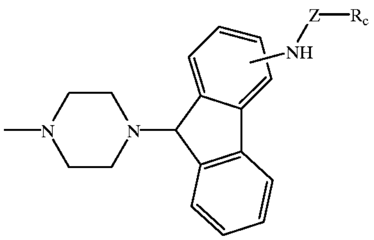

where Z is C(O) or $SO_2$ and $R_c$ is substituted or unsubstituted aryl, heteroaryl, arylalkyl, linear, branched or cyclic alkyl, arylamino, heteroarylamino, (arylalkyl)amino, or linear, branched or cyclic alkylamino. For example, $R_c$ can be, but is not limited to, thienyl, furanyl, benzyl, $C_3$–$C_6$-cycloalkyl, $C_1$–$C_6$-alkyl, isoxazolyl, $C_1$–$C_6$-alkylamino or substituted or unsubstituted phenylamino.

The present invention also relates to compounds of Formula II, (II)

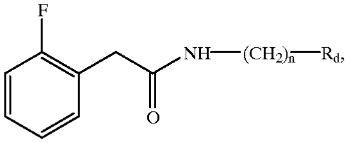

where n is 1 or 2 and $R_d$ is hydroxy, substituted or unsubstituted aryl, cycloalkyl, cycloalkenyl, heteroaryl, arylmethyl or diarylmethyl. Preferred substituents on these groups include one or more halogen atoms and $C_1$–$C_4$-alkoxy groups. In one embodiment, $R_d$ is phenyl or substituted phenyl, for example, 3-chlorophenyl, 4-chlorophenyl or 4-methoxyphenyl. Other suitable examples of $R_d$ include indolyl, cyclohexenyl, and diphenylmethyl.

The invention further relates to compounds of Formula III, (III)

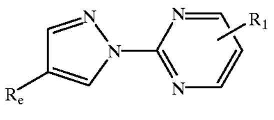

where $R_e$ is a substituted or unsubstituted phenyl group or a substituted or unsubstituted heteroaryl group and $R_l$ represents one or more substituents independently selected from hydrogen; halogen; trifluoromethyl; cyano; nitro; alkyl, preferably $C_1$–$C_6$-alkyl, more preferably $C_1$–$C_4$-alkyl and most preferably methyl; and alkoxy, preferably $C_1$–$C_6$-alkoxy, more preferably $C_1$–$C_4$-alkoxy and most preferably methoxy. In one embodiment, $R_l$ represents a single substituent, such as a fluorine, chlorine, bromine or iodine atom, or a trifluoromethyl group, bonded to carbon-4 of the pyrimidine ring, defined herein as one of the two pyrimidine carbon atoms adjacent one nitrogen atom. In one embodiment, $R_e$ is a phenyl group which is substituted with one or more substituents, preferably from 1 to 3 substituents independently selected from nitro; halogen, preferably chloro; alkoxy, preferably methoxy; and alkylsulfonyl, preferably methylsulfonyl. Examples of suitable substituted phenyl groups include 5-methoxy-2-nitrophenyl, 2-nitrophenyl, 4-chlorophenyl, 4-methylsulfonyl-2-nitrophenyl, 4-methoxyphenyl and 4-chloro-2-nitrophenyl. Preferred heteroaryl groups include substituted or unsubstituted pyrimidyl, pyrazyl, pyridyl, quinolyl, quinoxalyl and benzimidazolyl groups. In a preferred embodiment, the heteroaryl group is unsubstituted. For example, in this embodiment, $R_e$ can be selected from unsubstituted quinoxalyl, such as 2-quinoxalyl; pyrimidyl, such as 4-pyrimidyl; imidazolyl, such as 2-imidazolyl; pyridyl, such as 2-, 3- and 4-pyridyl, quinolyl, such as 2-quinolyl and 4-quinolyl, and pyrazyl, such as 2-pyrazyl.

In another embodiment, the present invention relates to compounds of Formula IV, (IV)

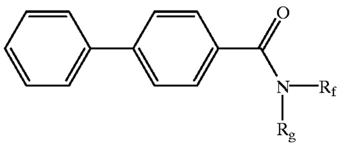

where $R_f$ and $R_g$ are each, independently, substituted or unsubstituted alkyl, substituted or unsubstituted arylalkyl or substituted or unsubstituted heteroarylalkyl. Examples of suitable identities for $R_f$ and $R_g$ include $C_1$–$C_6$-alkyl, preferably methyl; phenyl-$C_1$–$C_6$-alkyl, preferably phenyl-$C_1$–$C_2$-alkyl; and furanyl-$C_1$–$C_6$-alkyl, preferably furanyl-$C_1$–$C_2$-alkyl. $R_f$, $R_g$ and the nitrogen atom can also together form a substituted or unsubstituted five- or six-membered heterocyclic group. For example, $R_f$, $R_g$ and the nitrogen atom can form a substituted, or unsubstituted saturated, partially unsaturated or aromatic heterocyclic group. Preferred heterocyclic groups include substituted and unsubstituted piperidyl and piperazyl groups, for example, 1,2,7,8-terahydroisoquinolyl and 4-benzylpiperazyl.

The present invention further relates to compounds of Formula V, (V)

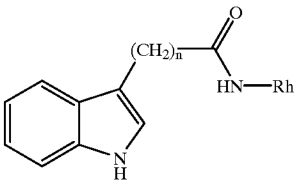

where n is 1, 2 or 3 and $R_h$ is substituted or unsubstituted alkyl, arylalkyl, alkenyl or cycloalkyl. Examples of suitable identities for $R_h$ include substituted and unsubstituted phenyl, substituted and unsubstituted phenyl-$C_1$–$C_6$-alkyl and substituted and substituted $C_2$–$C_{12}$-alkenyl. In a preferred embodiment, $R_h$ is selected from the group consisting of 3,5-dimethoxyphenyl-$C_1$–$C_2$-alkyl; 3,4-methylenedioxophenyl-$C_1$–$C_2$-alkyl; 4-pyrrolidylphenyl; 3,7-dimethyl-2,6-octadienyl and 2-isopropyl-bicylo[3.1.1]heptyl.

The invention also provides compounds of Formula VI, (VI)

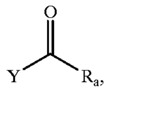

where $R_a$ has the meaning given in Formula I and Y is substituted or unsubstituted quinolyl, naphthyl, 4-, 6- or 7-indolyl, benzimidazolyl, benzotriazolyl, and heterocyclyphenyl, such as pyrrolidonylphenyl and pyrrolylphenyl. Suitable substituents include R, as defined above in Formula I. In one embodiment, Y is selected from among the groups shown below:

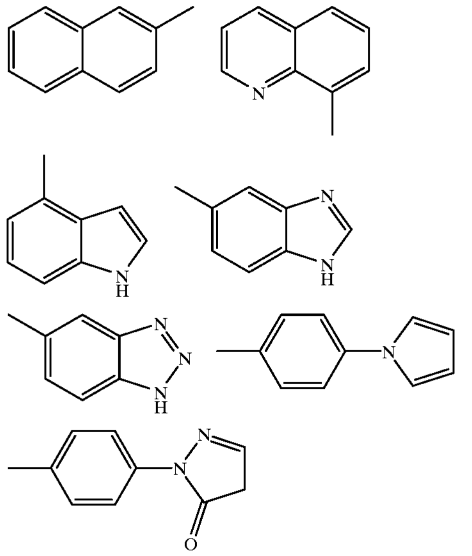

The present invention further relates to pharmaceutically acceptable salts of the compounds of Formulas I, II, III, IV and V. A "pharmaceutically acceptable salt" is a salt which retains the biological effectiveness and properties of the free base and which can be obtained by reaction with an inorganic or organic acid, such as hydrochloric acid, hydrobromic acid, sulfuric acid, nitric acid, phosphoric acid, organic sulfonic acid, organic carboxylic acid, organic phosphoric acid, for example, methanesulfonic acid, ethanesulfonic acid, p-toluenesulfonic acid, salicylic acid, lactic acid, tartaric acid and the like.

In another embodiment, the present invention relates to a method of treating a bacterial infection in a patient. The method comprises the step of administering to the patient a therapeutically effective amount of one or more compounds of Formulas I, II, III, IV or V, as described above. The patient to be treated can be any animal, and is preferably a mammal, such as a domesticated animal or a livestock animal. More preferably, the patient is a human.

The bacterial infection can be an infection by any bacterial species, and is particularly advantageous when used against bacteria which express an enoyl-ACP reductase. In one embodiment, the bacterial infection is an infection by a Gram negative bacterial species. Suitable Gram negative bacterial species include, but are not limited to, Bacteroides species, such as *B. fragilis*; Vibrio species, such as *V. cholerae*; Campylobacter species, such as *C. jejuni*; Helicobacter species, such as *H. pylori*; Pseudomonas species, such as *P. aeruginosa*; Haemophilus species, such as *H. influenzae*; Legionella species, such as *L. pneumophila*; Treponema species, such as *T. pallidum*; Borrelia species, such as *B. burgdorferi*; Bordatella species, such as *B. pertussis*; Neisseria species, such as *N. meningitidis* and *N. gonorrhoeae*; Shigella species, such as *S. sonnei*; Salmonella species, such as *S. typhimurium*; Yersinia species, such as *Y. enterocolitica* and *Y. pseudotuberculosis*; Klebsiella species, such as *K. pneumoniae*; Enterobactericiae, such as *Escherichia coli*, including enterotoxigenic, enteropathogenic, enteroinvasive, enterohemorhagic and enteroaggregative *E. coli* strains.

Preferably, the bacterial infection is an infection by a Mycobacterial species, such as an infection by a pathogenic Mycobacterial species. Such pathogenic Mycobacterial species include, but are not limited to, *Mycobacterium*

*tuberculosis, Mycobacterium avian-intracellulare, Mycobacterium kansasii, Mycobacterium bovis, Mycobacterium africanum, Mycobacterium genavense, Mycobacterium leprae, Mycobacterium xenopi, Mycobacterium simiae, Mycobacterium scrofulaceum, Mycobacterium malmoense, Mycobacterium celatum, Mycobacterium abscessus, Mycobacterium chelonae, Mycobacterium szulgai, Mycobacterium gordonae, Mycobacterium haemophilum, Mycobacterium fortuni* and *Mycobacterium marinum.*

In one embodiment, the Mycobacterial infection is an infection by *Mycobacterium tuberculosis*. In this embodiment, the infection can be, for example, a latent or dormant infection, in which the patient exhibits no symptoms due to the *M. tuberculosis* infection, or the patient can have active tuberculosis. In most people who are infected with *M. tuberculosis*, the bacterium is limited to the cells which line the air sacs of the lungs. In certain individuals, such as those weakened by age, illness, for example, HIV infection or AIDS, malnutrition or immunosuppressive chemotherapy, such dormant infections can give rise to active tuberculosis, and the infection can become contagious. The present method can be used, for example, to rid an individual of a dormant *M. tuberculosis* infection, and thereby provide prophylaxis against the development of active tuberculosis. The method can also be used to treat a patient having active tuberculosis.

A "therapeutically effective amount" is an amount of a compound of Formula I, II, III, IV or V, or a combination of two or more such compounds, which inhibits, totally or partially, the progression of the condition or alleviates, at least partially, one or more symptoms of the bacterial infection. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

The compound or compounds of Formulas I, II, III, IV or V can be administered alone or in combination with one or more additional therapeutic agents, as can be selected by one skilled in the art, such as, for example, one or more antimicrobial agents. For example, one or more compounds of Formulas I, II, III, IV or V can be administered in combination with one or more agents, such as antimicrobial agents, which can be employed in the treatment of the bacterial infection. Suitable agents of this type are known in the art and include isoniazid, rifampin, pyrazinamide, ethambutol, streptomycin, p-aminosalicyclic acid, clarithromycin, clofazimine, minocycline, sulfonamides, ethionamide, cycloserine, kanamycin, amikacin, capreomycin, viomycin, thiacetazone, rifabutin and the quinolones, such as ciprofloxacin, ofloxacin and sparfloxicin.

In one embodiment, the bacterial infection is an infection by *Mycobacterium tuberculosis* and the compound or compounds of Formula I, II, III, IV or V are administered in combination with one or more agents which are known in the art for the treatment of tuberculosis. For example, the compound or compounds of the invention can be administered in combination with one or more drugs selected from the group consisting of isoniazid, rifampin, pyrazinamide, ethambutol, streptomycin, p-aminosalicyclic acid, ethionamide, cycloserine, kanamycin, amikacin, capreomycin, viomycin, thiacetazone, rifabutin and the quinolones, such as ciprofloxacin, ofloxacin and sparfloxicin.

When two or more compounds of the invention are administered in combination, they can be administered simultaneously, sequentially or separately, for example, with administration of each agent or two or more groups of agents separated by a suitable time interval, such as hours. When the compound or compounds of the invention are administered in combination with one or more additional agents, such as are discussed above, the compound or compounds of the invention can be, and the additional agents or agents can be administered simultaneously, sequentially or separately, for example, with administration of each agent or two or more groups of agents separated by a suitable time interval, such as hours.

The compounds of this invention can be administered to a human patient by themselves or in pharmaceutical compositions where they are mixed with suitable carriers or excipient(s) at doses to treat or ameliorate vascular hyperpermeability, edema and associated disorders. Mixtures of these compounds can also be administered to the patient as a simple mixture or in suitable formulated pharmaceutical compositions. Techniques for formulation and administration of the compounds of the instant invention can be found in "Remington: the Science and Practice of Pharmacy," $19_{th}$ edition, Mack Publishing Co., Easton, Pa. (1995).

Suitable routes of administration can, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one can administer the compound in a local rather than a systemic manner, for example, via injection of the compound directly into an edematous site, often in a depot or sustained release formulation. The compound can also be administered topically. For example, an infected tissue can be exposed, such as via an incision, and the compound can be applied to the surface of the tissue.

Furthermore, one can administer the drug in a targeted drug delivery system, including, for example, a liposome coated with an antibody specific for the target tissue.

The pharmaceutical compositions of the present invention can be manufactured in a manner that is itself known, for example, by means of conventional mixing, dissolving, granulating, dragee-making, levigating, emulsifying, encapsulating, entrapping or lyophilizing processes.

Pharmaceutical compositions for use in accordance with the present invention thus can be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention can be formulated in aqueous solutions, preferably in physiologically compatible buffers such as Hanks' solution, Ringers solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of a suitable material, such as, for example, gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration by injection, e.g. bolus injection or continuous infusion. Formulations for injection can be presented in unit dosage form, e.g.in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions.

Alternatively, the active ingredient can be in powder form for constitution with a suitable vehicle, for example, sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly or by intramuscular injection). Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in the method of the invention, the therapeutically effective dose can be estimated initially from in vitro assays and animal models. For example, a dose can be formulated in cellular and animal models to achieve a circulating concentration range that includes the $IC_{50}$ as determined in cellular assays (i.e., the concentration of the test compound which achieves a half-maximal inhibition of InhA activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit InhA activity in intact bacterial cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, for example, Ross in "Goodman and Gilman's The Pharmacological Basis of Therapeutics", Gilman et al., ed. Chapter 2 (1990) and Benet et al. in "Goodman and Gilman's The Pharmacological Basis of Therapeutics", Gilman et al., ed. Chapter 1 (1990)). In the treatment of crises, the administration of an acute bolus or an infusion approaching the MTD may be required to obtain a rapid response.

Dosage amount and interval can be adjusted individually to provide plasma levels of the active moiety which are sufficient to maintain the desired effects, or minimal effective concentration (MEC). The MEC will vary for each compound but can be estimated from in vitro data; e.g. the concentration necessary to achieve 50–90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90% until the desired amelioration of symptoms is achieved. In cases of local administration or selective uptake, the effective local concentration of the drugcan not be related to plasma concentration.

The amount of composition administered will, of course, be dependent on the subject being treated, on the subject's weight, the severity of the affliction, the manner of administration and the judgment of the prescribing physician.

EXAMPLES

Example 1

Synthesis of N-[2-(4-Chlorophenyl)-ethyl]-2-(2-fluorophenyl)acetamide (compound 1)

2-Fluorophenylacetic acid (17 mg, 0.11 mmole) and 4-chlorophenethylamine (15 mg, 0.1 mmole) were dissolved in 5 ml dichloromethane. To this was added catalytic 4-dimethylaminopyridine (DMAP) and 1-(3-dimethylaminopropyl)-3-ethylcarbodiimide hydrochloride (EDCI, 33 mg, 0.11 mmole). The resulting solution was stirred at room temperature overnight. The reaction was then worked up by washing sequentially with 1N HCl, saturated sodium bicarbonate, and saturated sodium chloride. The compound was then purified by flash chromatography on silica gel (40:1 $CHCl_3$/MeOH). $^1$H NMR (300 Mhz, $CDCl_3$) δ 7.31–6.92 (m, 8H), 5.48 (bs, 1H), 3.51 (s, 2H), 3.42 (m, 2H), 2.70 (m, 2H).

Example 2

2 Synthesis of N-(3, 7-Dimethyl-octa-2,6-dienyl)-3-(1H-indol-3-yl)-propionamide (compound 2)

Indole-3-propionic acid (10 mg, 0.5285 mmole) and geranylamine (85 mg, 0.4805 mmole) were dissolved in 10 ml dichloromethane. To this was added catalytic DMAP and EDCI (157 mg, 0.5285 mmole) in 5 ml dichloromethane and the resulting solution was stirred at room temperature overnight. The reaction was worked up by washing sequentially with 1N HCl, saturated sodium bicarbonate, and saturated sodium chloride. The compound was then purified by flash chromatography on silica gel (40:1 $CHCl_3$/MeOH). $^1$H NMR (300 Mhz, $CDCl_3$) δ 8.23 (bs, 1H), 7.59 (d, 1H), 7.35 (d, 1H), 7.21–7.08 (m, 2H), 6.97 (s, 1H), 5.29 (bs, 1H), 5.02 (m, 2H), 3.78 (m, 2H), 3.10 (t, 2H), 2.51 (t, 2H), 2.18–1.88 (m, 4H), 1.77–1.48 (m, 9H).

Example 3

Synthesis of 2-[4-(2,4-dinitrophenyl)-pyrazol-1-yl]4-trifluoromethyl pyrimidine (compound 3)

An equimolar mixture of 2,4-dinitrophenyl malondialdehyde and 2-hydrazino-4-(trifluoromethyl)pyrimidine were heated to 70° C. in dimethylsulfoxide, ethanol, or dioxane-ethanol containing catalytic p-toluenesulfonic acid. The reaction was allowed to stir for 16 hours. The solution was then concentrated and dissolved in ethyl acetate. This solution was then washed with 1M HCl, saturated sodium bicarbonate and saturated sodium chloride. The organic layer was then dried over MgSO4. The sample was then purified by flash chromatography (1:1 ethyl acetate/hexane) on silica gel. 1H NMR (300 Mhz, CDCl3/acetone-d6) δ 9.19 (d, 1H), 8.91 (s, 1H), 8.72 (d, 1H), 8.49 (dd, 1H), 8.02 (s, 1H), 7.82 (d, 1H), 7.63 (d, 1H).

Example 4

Synthesis of 1-[1-(1H-Indole-5-carbonyl)-4-phenyl-piperidin-4-yl]-butan-1-one (compound 4)

Indole-5-carboxylic acid (177 mg, 1.1 mmole) and 4-butyryl-4-phenylpiperidine (231 mg, 1.0 mmole) were dissolved in 10 ml dichloromethane. To this solution was added catalytic DMAP and EDCI (330 mg, 1.1 mmole). The resulting solution was then stirred at room temperature overnight. The reaction was worked up by washing sequentially with 1N HCl, saturated sodium bicarbonate, and saturated sodium chloride. The compound was then purified by flash chromatography on silica gel (40:1 $CHCl_3$/MeOH). $^1$H NMR (300 Mhz, $CDCl_3$) δ 8.60 (s, 1H), 7.66 (d, 1H), 7.38–7.18 (m, 8H), 6.53 (d, 1H), 4.28 (bs, 1H), 3.67 (bs, 1H), 3.39 (t, 2H), 2.42 (bs, 2H), 2.18 (m, 3H), 1.88 (bs, 1H), 1.41 (m, 2H), 0.66 (t, 3H).

Example 5

Synthesis of [4-(4-Chlorobenzoyl)-piperidin-1-yl]-(1H-indol-5-yl)-methanone (compound 5)

Indole-5-carboxylic acid (18 mg, 0.11 mmole) and 4-(4-chlorobenzoyl) piperidine hydrochloride (26 mg, 0.1 mmole) were dissolved in 5 ml dichloromethane. To this solution was added triethylamine (1 eq. to neutralize the HCl salt) catalytic DMAP and EDCI (33 mg, 0.11 mmole). The reaction mxture was stirred at room temperature overnight and then worked up by washing sequentially with 1N HCl, saturated sodium bicarbonate, and saturated sodium chloride. The compound was then purified by flash chromatography on silica gel (40:1 $CHCl_3$/MeOH). $^1$H NMR (300 Mhz, $CDCl_3$) δ 8.45 (s, 1H), 7.88 (d, 2H), 7.72 (s, 1H), 7.45 (d, 2H), 7.38 (d, 1H), 7.24 (s, 2H), 6.58 (s, 1H), 3.42 (m, 1H), 3.11 (m, 2H), 1.83 (m, 4H), 1.60 (m, 2H).

Example 6

[4-(9H-Fluoren-9-yl)-piperazin-1-yl]-(1H-indol-5-yl)-methanone (compound 6)

Indole-5-carboxylic acid (17 mg, 0.11 mmole) and N-9-fluorenyl-piperazine dihydrochloride (32 mg, 0.1 mmole) were dissolved in 5 ml dichloromethane. To this solution was added triethylamine (2 eq. to neutralize HCl salt), catalytic DMAP and EDCI (33 mg, 0.11 mmole). The resulting mixture was stirred at room temperature overnight and was then worked up by washing sequentially with 1N HCl, saturated sodium bicarbonate, and saturated sodium chloride. The product was then purified by flash chromatography on silica gel (40:1 $CHCl_3$/MeOH). $^1$H NMR (300 Mhz, $CDCl_3$) δ 8.38 (s, 1H), 7.72–7.60 (m, 5H), 7.40–7.18 (m, 7H), 6.55 (d, 1H), 4.88 (s,1H), 3.60 (bs, 4H), 2.62 (bs, 4H).

Example 7

Synthesis of [4-(9H-(2-trifluoroacetamido)-fluoren-9-yl)-piperazin-1-yl]-(1H-indol-5-yl)-methanone (compound 7)

t-Butyl-1-piperazine carboxylate (593 mg, 302 mmole) and 9-bromo-2-trifluoroacetamido fluorene (1031 mg, 2.9 mmole) were dissolved in 15 ml chloroform. Added sodium carbonate hydrate (718 mg, 5.8 mmole) dissolved in 2 ml water. The reaction was heated to reflux for 16 hours and then was worked up by washing with water, saturated sodium chloride and drying over $MgSO_4$. The residue was recrystalized from ethyl acetate/hexane. $^1$H NMR (300 Mhz, $CDCl_3$) δ 7.82 (s, 1H), 7.63–7.52 (m, 5H), 7.30–7.19 (m, 2H), 4.79 (s, 1H), 3.30 (bs, 4H), 2.45 (bs, 4H), 1.36 (s, 9H).

N-9-(2-trifluoroacetamido)-fluorenyl-piperazine 4-(2-trifluoroacetamido)-9H-fluoren-9-ylpiperazine-1-carboxylic acid t-butyl ester (1330 mg, 2.9 mmole) was dissolved in 10 ml dichloromethane. To this solution was added trifluoroacetic acid (2.3 ml, 29 mmole) dissolved in 3 ml dichloromethane. After 2 hours, the solvent was removed in vacuo and the residue was redissolved in 20 ml dichloromethane. This solution was washed with aqueous potassium carbonate until neutral, then with saturated sodium chloride and dried over $MgSO_4$. Solvent was then removed in vacuo, and the residue was recrystallized from ethyl acetate/hexane. $^1$H NMR (300 Mhz, $CDCl_3$) δ 7.76–7.71 (m, 2H), 7.62–7.54 (m, 3H), 7.32–7.19 (m, 2H), 4.75 (s, 1H), 3.38 (bs, 1H), 2.75 (m, 4H), 2.52 (m, 4H).

[4-(9H-(2-tifluoroacetamido)-fluoren-9-yl)-piperazin-1-yl]-(1H-indol-5-yl)-methanone Indole-5-carboxylic acid (211 mg, 1.31 mmole) and N-9-(2-trifluoroacetamido)-fluorenyl-piperazine (430 mg, 1.19 mmole) were dissolved in 20 ml dichloromethane containing 3 ml DMSO. To this solution was added catalytic DMAP and EDCI (389 mg, 1.31 mmole) in 5 ml dichloromethane. The resulting solution was stirred at room temperature overnight, then the reaction was worked up by washing sequentially with 1N HCl, saturated sodium bicarbonate, and saturated sodium chloride. The compound was then purified by flash chromatography on silica gel (40:1 $CHCl_3$/MeOH). $^1$H NMR (300 Mhz, $CDCl_3$) δ 9.72 (s, 1H), 9.19 (s, 1H), 7.83 (s, 1H), 7.65–7.53 (m, 5H), 7.37 (t, 1H), 7.25 (t, 1H), 7.14–7.03 (m, 3H), 6.40 (s, 1H), 4.64 (s, 1H), 3.85–3.20 (bd, 4H), 2.75–2.25 (bd, 4H).

Example 8

Synthesis of [4-(9H-(2-amino)-fluoren-9-yl)-piperazin-1-yl]-(1H-indol-5-yl)-methanone (compound 8)

[4-(9H-(2-trifluoroacetamido)-fluoren-9-yl)-piperazin-1-yl]-(1H-indol-5-yl)-methanone (535 mg, 1.06 mmole) was dissolved in 25 ml methanol. To this solution was added potassium carbonate (575 mg, 4.17 mmole) dissolved in 3 ml water. The solution was then stirred at room temperature for 16 hours, at which time a white solid had precipitated out of solution. This solid was isolated by filtration, washed with cold methanol and dried under vacuum. $^1$H NMR (300 Mhz, $CDCl_3$) δ 8.58 (s, 1H), 7.65 (s, 1H), 7.58–7.42 (m, 3H), 7.37–7.24 (m, 2H), 7.19 (m, 3H), 6.98 (s, 1H), 6.68 (dd, 1H), 6.49 (s, 1H), 4.78 (s, 1H), 3.95–3.40 (bd, 4H), 3.05–2.15 (bd, 4H).

Example 9

Synthesis of 1-(2-Chlorophenyl)-3-{9-[4-(1H-indole-5-carbonyl)-piperazin-1-yl]-9H-fluoren-2-yl}-urea (compound 9)

N-(2-amino)-9-fluorenyl-piperazine indole (14 mg, 0.034 mmole) was dissolved in 4 ml dichloromethane. To this solution was added catalytic DMAP and then 2-chlorophenyl isocyanate (11 mg, 0.068 mmole). The resulting solution was stirred at room temperature overnight and an off-white precipitate formed. The precipitate was collected by filtration, washed with cold dichloromethane and dried under vacuum. 1H NMR (300 Mhz, $CDCl_3$/$CD_3OD$) δ 8.10 (d, 1H), 7.65 (s, 1H), 7.48 (m, 4H), 7.37 (d 1H), 7.24 (m, 3H), 7.14 (m, 3H), 7.03 (d, 1H), 6.84 (t, 1H), 6.38 (s, 1H), 4.75 (s,1H), 3.80–3.20 (bd, 4H), 2.84–2.25 (bd, 4H).

Example 10

InhA inhibition assay

InhA Assay

InhA activity in the presence of octenoyl-CoA and NADH was determined using a continuous assay in which the rate of consumption of NADH was measured by the decrease in absorbance at 340 nM.

Materials and Methods

All the assays were run in 96-well plates and read on a Tecan-SLT Lab instruments 340 ATTC plate reader. Components were added to assay wells A3 through H12 in the following order: 40 μl of sample (200 μM in 4% DMSO, 0.2% P104; final concentration in the assay is 40 μM), then 10 μl of 1×assaybuffer Pipes pH 6.8, 50 mM). In wells E1 through H1 50 μl of palmitoyl-CoA was added (final concentration=375 μM); this compound was used as a standard inhibitor. To all of the wells 50 μl of octenoyl-CoA (1 mM in 1×assaybuffer) was added (final concentration=250 μM; Km=7, 18 μM). After that 50 μl of NADH (400 μM) was added (final concentration=100 μM, Km=580 μM).

50 μl of 1×assay buffer was added to wells A1 through D1 as a blank (0% activity). To all the wells except the blank 50 μl of an InhA dilution was added to give a linear range in $A_{340}$ of −20 mOD/min. The plate was put on a plate shaker for 20 seconds and the absorbance at 340 nM was measured for 10 minutes.

A percentage inhibition together with standard deviation was calculated by comparing the data obtained for the samples (in duplicate) with the data for enzyme alone which (wells A2 through H2, the 100% control). The internal standard for every plate was palmitoyl-CoA which gave about 40% inhibition at 375 uM.

For the most active compounds of IC50 (inhibitory concentration of 50%) was determined. It was determined that by using a series of dilutions such that inhibition varied from >70% to <20%. A curve was fit to this data and the concentration yielding 50% inhibition was determined analytically from the curve.

The results of the InhA inhibition assay are presented in Tables 1–6 below.

TABLE 1

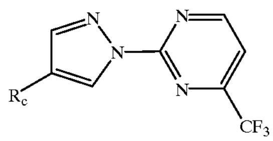

| Compound Number | $R_c$ | Percentage Inhibition (@ 40 μM) |
|---|---|---|
| 10 | 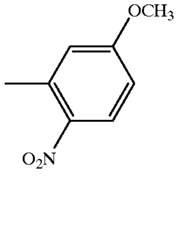 | 17 |

TABLE 1-continued
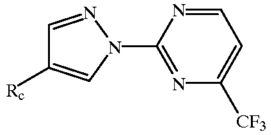
| Compound Number | $R_c$ | Percentage Inhibition (@ 40 $\mu$M) |
|---|---|---|
| 11 | 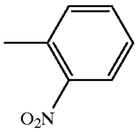 | 14 |
| 12 | 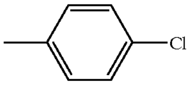 | 8 |
| 13 | 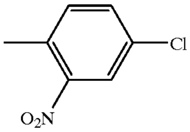 | 82 |
| 14 | 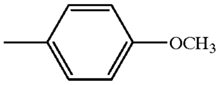 | 4 |
| 15 | 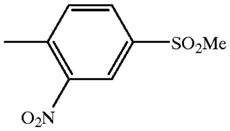 | 10 |
| 16 | 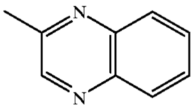 | 36 |
| 17 | 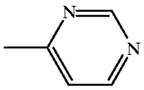 | 36 |
| 18 | 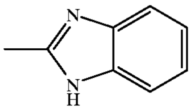 | 36 |
| 19 | 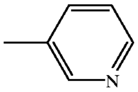 | 36 |
| 20 | 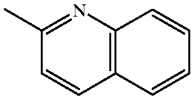 | 16 |
TABLE 1-continued
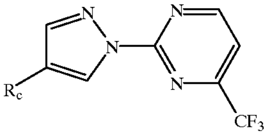
| Compound Number | $R_c$ | Percentage Inhibition (@ 40 $\mu$M) |
|---|---|---|
| 21 | 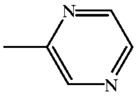 | 9 |
| 22 | 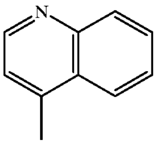 | 9 |
TABLE 2
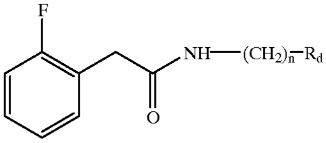
| Compound Number | $-(CH_2)_n-R_d$ | Percentage Inhibition (@ 40 $\mu$M) |
|---|---|---|
| 23 | 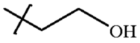 | 34 |
| 24 | 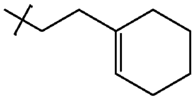 | 56 |
| 25 | 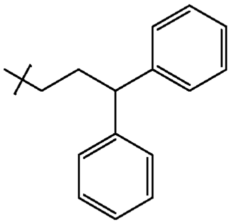 | 63 |
| 26 | 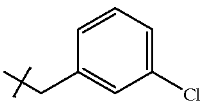 | 75 |
| 27 | 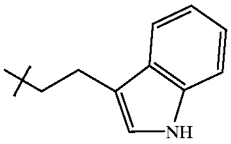 | 47 |

TABLE 2-continued
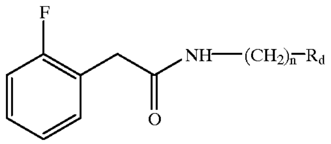
| Compound Number | $-(CH_2)_n-R_d$ | Percentage Inhibition (@ 40 $\mu$M) |
|---|---|---|
| 28 | 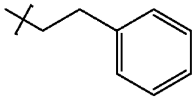 | 45 |
| 1 | 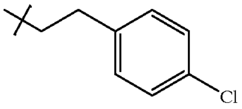 | 82 |
| 29 | 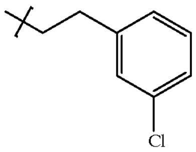 | 84 |
| 30 | 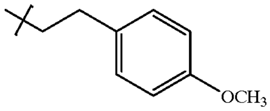 | 63 |
TABLE 3
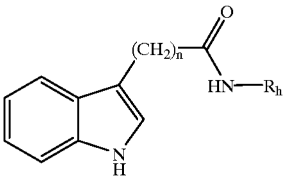
| Compound Number | n, $R_h$ | | Percentage Inhibition (@ 40 $\mu$M) |
|---|---|---|---|
| 31 | 3 | 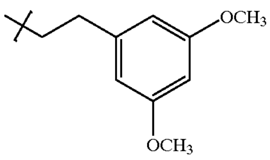 | 21 |
| 2 | 3 | 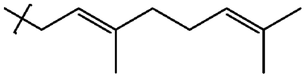 | 51 |
| 32 | 3 | 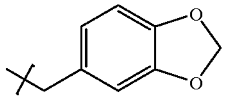 | 37 |
TABLE 3-continued
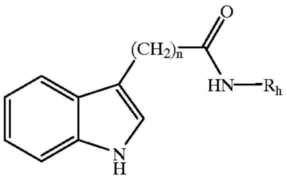
| Compound Number | n, $R_h$ | | Percentage Inhibition (@ 40 $\mu$M) |
|---|---|---|---|
| 33 | 3 | 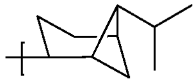 | 34 |
| 34 | 3 | 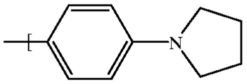 | 28 |
| 35 | 2 | 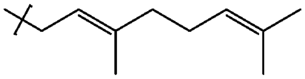 | 73 |
| 36 | 2 | 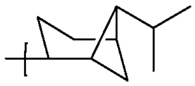 | 28 |
TABLE 4
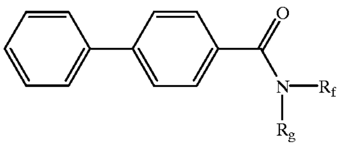
| Compound Number | $N(R_f)R_g$ | Percentage Inhibition (@ 40 $\mu$M) |
|---|---|---|
| 37 | 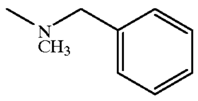 | 44 |
| 38 | 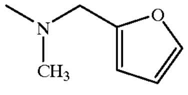 | 29 |
| 39 | 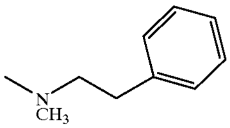 | 32 |
| 40 | 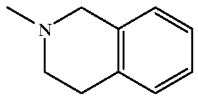 | 27 |

TABLE 4-continued
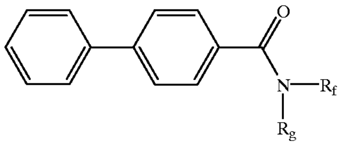
| Compound Number | $N(R_f)R_g$ | Percentage Inhibition (@ 40 $\mu$M) |
|---|---|---|
| 41 | 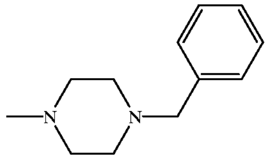 | 27 |
TABLE 5
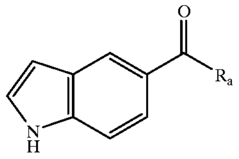
| Com-pound Number | $R_a$ | Percentage Inhi-bition (@ 40 $\mu$M) |
|---|---|---|
| 42 | 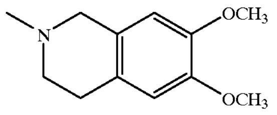 | 86 |
| 43 | 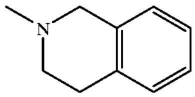 | 86 |
| 44 | 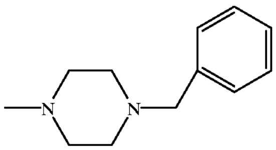 | 62 |
| 45 | 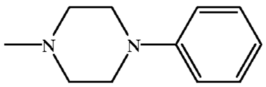 | 73 |
| 46 | 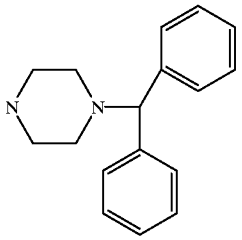 | 106 |
TABLE 5-continued
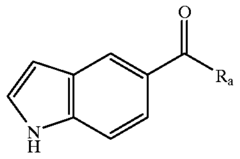
| Com-pound Number | $R_a$ | Percentage Inhi-bition (@ 40 $\mu$M) |
|---|---|---|
| 47 | 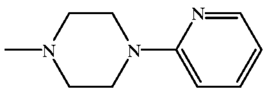 | 36 |
| 48 | 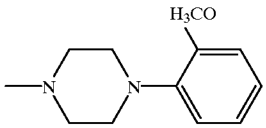 | 78 |
| 49 | 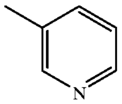 | 36 |
| 50 | 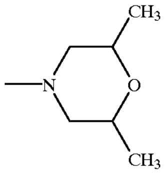 | 47 |
| 51 | 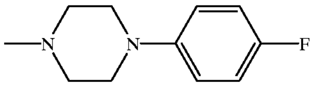 | 53 |
| 52 | 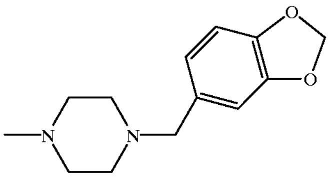 | 51 |
| 53 | 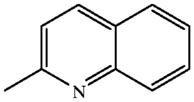 | 16 |

TABLE 6

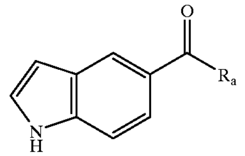

| Compound Number | $R_a$ | Percentage Inhibition (@ 40 μM) |
|---|---|---|
| 54 | 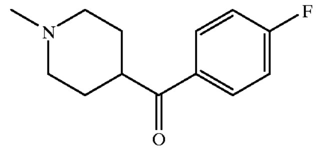 | 84 |
| 55 | 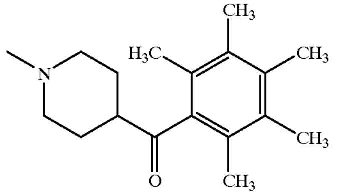 | 78 |
| 5 | 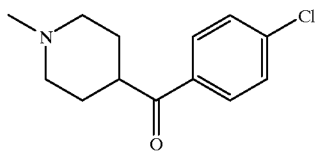 | 97 |

Example 11

A freeze-dried culture of the Bacillus Calmet-Guerin (BCG), Pasteur strain, of *Mycobacterium bovis* (Karlson and Lessel) was obtained from the American Type Culture Collection (ATCC-35734). The lyophilized pellet (in nonfat milk) was resuspended in 0.3 ml of Middlebrook 7H9 broth (ATCC culture medium 173; SP/Baxter #11417*BT) and diluted to 5 ml with 7H9 broth containing 10% OADC (SP/Baxter BB11886) supplement (7H9-OADC broth). Dilutions of 1/10 were performed to $10^7$. The liquid cultures were incubated with shaking at 37° C. in screw cap tubes with the lids closed.

The highest concentration of liquid culture was streaked onto Middlebrook 7H10 agar (SP/Baxter #11422*BT) containing 10% OADC supplement (7H10-OADC agar) in a petri plate or stabbed onto Lowenstein-Jensen medium (ATCC culture medium 90) in a slant tube (BBL 4320908) or a Mycoflask™ (BBL 21115) and propagated at 37° C. with the lids closed. The OADC supplement is heat sensitive and is added to the melted 7H10 agar before solidification, Colonies of BCG form a dense, waxy mass (in liquid or on agar) which must be homogenized in 7H9-OADC broth in a sterile Dounce homogenizer to generate an even suspension. Frozen stocks of BCG were prepared by homogenization of BCG masses (2–4 mm) in 10 ml of 7H9-OADC broth. One ml aliquots in freezer vials were stored at −80° C.

Drug sensitivity of BCG growth was performed in 24 well plates containing 2 ml of 7H10-OADC agar per well and dilutions of test compounds or control drugs ranging from 25 μM to 1 nM. All compounds and drugs were diluted into liquid agar from initial 5 mM stocks dissolved in DMSO. No inhibition of BCG growth was seen at the highest concentration of DMSO (0.5%).

Inocula of BCG were prepared from macroscopic colonies (1–2 mm in diameter) on Lowenstein-Jensen medium (slants or Mycoflasks) or from liquid culture and homogenized in 2 ml of 7H9-OADC broth. Individual wells of 24 well plates were inoculated with 10 μl after the 7H10-OADC agar had solidified.

Colony growth was observable after 8 days, depending on the amount of the initial inoculum. Growth of single colonies to observable size on agar from a $10^7$ dilution required incubation times from 30 to 60 days. All plate incubations were performed inside closed Zip-lock bags to prevent excessive moisture loss during the extended incubations.

Control drugs, ethambutol dihydrochloride, isoniazid (isonicotinic acid hydrazide), and rifampicin were obtained from Sigma Chemical Co.

Results

The control drugs: ethambutol dihydrochloride, isoniazid, and rifampicin were found to have $IC_{50}$'s for BCG growth of 10 μM, 3 μM, and 10 nM, respectively. Results for these and the test compounds are shown in Tables 7–9 below.

TABLE 7

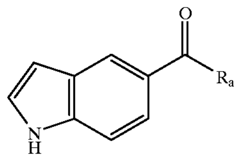

| Compound Number | $R_a$ | IC50 (μM) |
|---|---|---|
| 56 | 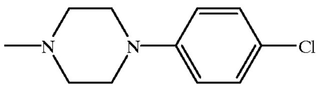 | 4.2 |
| 57 | 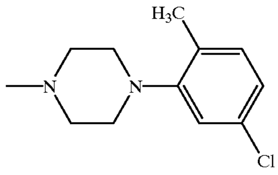 | 1.04 |
| 58 | 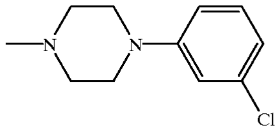 | 1.21 |
| 59 | 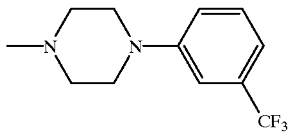 | 1.89 |

TABLE 7-continued
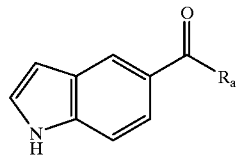
| Compound Number | $R_a$ | IC50 ($\mu$M) |
|---|---|---|
| 4 | 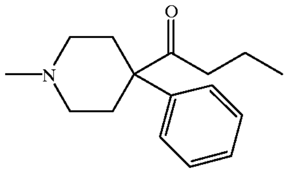 | 0.23 |
TABLE 8
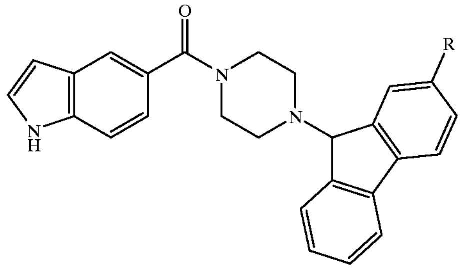
| Compound Number | R | IC50 ($\mu$M) |
|---|---|---|
| 60 | 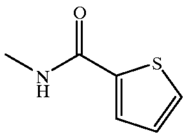 | 0.695 |
| 61 | 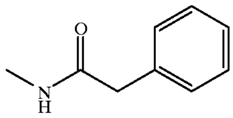 | 0.585 |
| 62 | 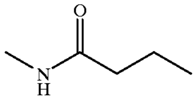 | 0.455 |
| 63 | 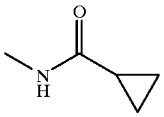 | 1.012 |
| 64 | 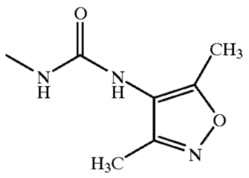 | 0.383 |
TABLE 8-continued
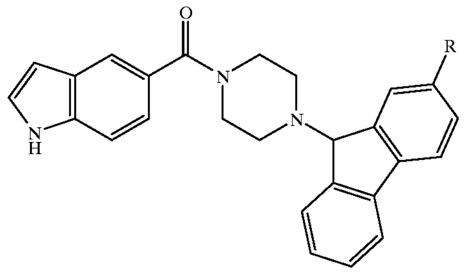
| Compound Number | R | IC50 ($\mu$M) |
|---|---|---|
| 65 | 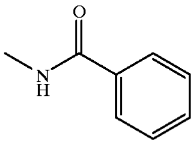 | 0.741 |
| 66 | 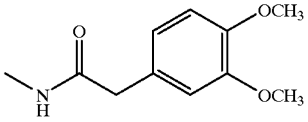 | 0.436 |
| 67 | 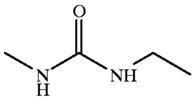 | 0.475 |
| 68 | 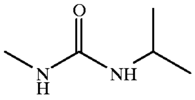 | 0.328 |
| 9 | 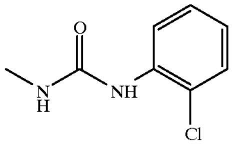 | 0.247 |
| 69 | 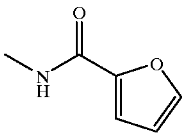 | 0.678 |
| 70 | H | 0.155 |

TABLE 9

| Compound | InhA IC-50 | BCG Growth IC-50 | Cell Tox (m. Embryo) | Cell Tox (h. Kidney) | Cell Tox (h. Lung) |
|---|---|---|---|---|---|
| 35 | | >25 μM | 11–90 μM | 41–62 μM | 11–48 μM |
| 4 | | >25 μM | 46–50 μM | 23–48 μM | 33–50 μM |
| 70 | 0.16–0.34 μM | 8.3 μM | 46–52 μM | 35–44 μM | 24–48 μM |
| 71 | 0.12 μM | 8.3 μM | 23 μM | 28 μM | 37 μM |
| 72 | 0.13 μM | 2.8 μM | 23 μM | 29 μM | 34 μM |
| 73 | 0.12 μM | 6.2 μM | | | |
| ethambutol | | 10 μM | | | |
| isoniazid | | 3 μM | | | |
| rifampicin | | 0.01 μM | | | |

71 = 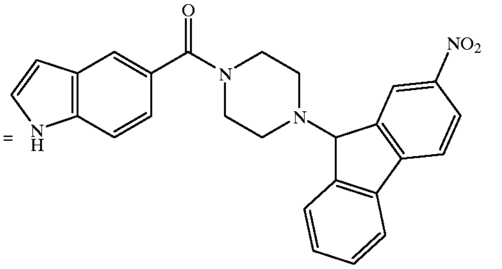

72 = 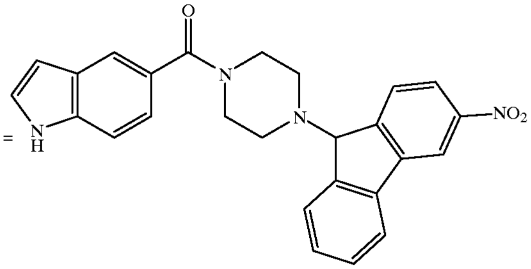

73 = 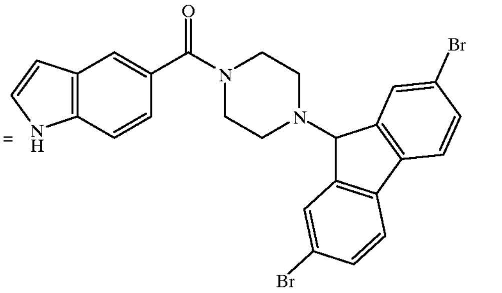

While this invention has been particularly shown and described with references to preferred embodiments thereof, it will be understood by those skilled in the art that various changes in form and details can be made therein without departing from the scope of the invention encompassed by the appended claims.

What is claimed is:

1. A compound of Formula III, (III)

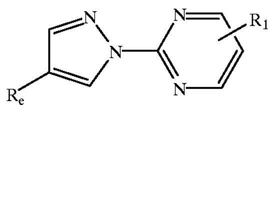

or a salt thereof with a pharmaceutically acceptable acid, wherein $R_e$ is a substituted or unsubstituted phenyl group or a substituted or unsubstituted heteroaryl group; and $R_l$ represents one or more substituents independently selected from the group consisting of alkoxy, cyano, nitro and trifluoromethyl, provided that the compound is not 2-[4-(2-nitro-4-chlorophenyl)-pyrazol-1-yl]-4-trifluoromethyl pyrimidine.

2. The compound of claim 1 wherein $R_e$ is a substituted or unsubstituted pyrimidyl, pyrazyl, pyridyl, quinolyl, quinoxalyl or benzimidazolyl group.

3. The compound of claim 2 wherein $R_e$ is 2-quinoxalyl, 4-pyrimidyl, 2-benzimidazolyl; 2-, 3- or 4-pyridyl, 2-quinolyl, 4-quinolyl and 2-pyrazyl.

4. A compound of Formula III, (III)

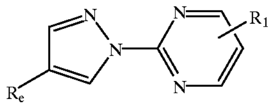

or a salt thereof with a pharmaceutically acceptable acid, wherein $R_e$ is a phenyl group which is substituted with one or more substituents independently selected from the group consisting of nitro, alkoxy, and alkylsulfonyl; and $R_l$ represents one or more substituents independently selected from the group consisting of alkoxy, cyano, nitro and trifluoromethyl.

5. The compound of claim 4 wherein $R_e$ is selected from the group consisting of 5-methoxy-2-nitrophenyl, 2-nitrophenyl, 4-methylsulfonyl-2-nitrophenyl and 4-methoxyphenyl.

6. A compound of Formula III, (III)

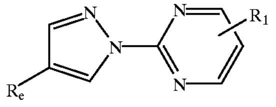

or a salt thereof with a pharmaceutically acceptable acid, wherein $R_e$ is a substituted phenyl group, wherein the phenyl group is substituted with one or more substituents wherein at least one substituent is selected from the group consisting of nitro and alkylsulfonyl; a substituted heteroaryl group; or an unsubstituted heteroaryl group, wherein the unsubstituted heteroaryl group is not pyridyl; and $R_l$ represents one or more substituents independently selected from the group consisting of hydrogen, halogen, alkyl, alkoxy, cyano, nitro and trifluoromethyl, provided that the compound is not 2-[4-(2-nitro-4-chlorophenyl)-pyrazol-1-yl]-4-trifluoromethyl pyrimidine.

7. A compound of Formula III, (III)

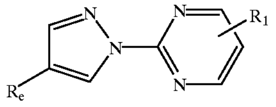

or a salt thereof with a pharmaceutically acceptable acid, wherein $R_e$ is a substituted or unsubstituted phenyl group or a substituted or unsubstituted heteroaryl group; and $R_l$ represents trifluoromethyl.

8. A compound represented by the following structural formula:

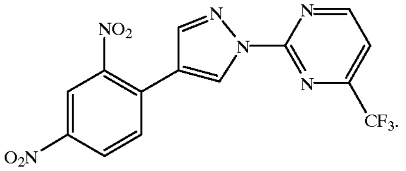

9. A method of treating a Mycobacterial infection in a patient, comprising the step of administering to the patient a therapeutically effective amount of one or more compounds of Formula III, (III)

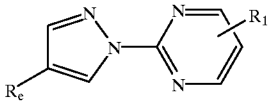

or a salt thereof with a pharmaceutically acceptable acid, wherein $R_e$ is a substituted phenyl group, wherein the phenyl group is substituted with one or more substituents wherein at least one substituent is selected from the group consisting of nitro and alkylsulfonyl; a substituted heteroaryl group; or an unsubstituted heteroaryl group, wherein the unsubstituted heteroaryl group is not pyridyl; and $R_l$ represents one or more substituents independently selected from the group consisting of hydrogen, halogen, alkyl, alkoxy, cyano, nitro and trifluoromethyl, provided that the compound is not 2-[4-(2-nitro-4-chlorophenyl)-pyrazol-1-yl]-4-trifluoromethyl pyrimidine.

10. The method of claim 9 wherein the Mycobacterial infection is an infection by a Mycobacterial species selected from the group consisting of *Mycobacterium tuberculosis, Mycobacterium avian-intracellulare, Mycobacterium kansasii, Mycobacterium bovis, Mycobacterium africanum, Mycobacterium genavense, Mycobacterium leprae, Mycobacterium xenopi, Mycobacterium simiae, Mycobacterium scrofulaceum, Mycobacterium malmoense, Mycobacterium celatum, Mycobacterium abscessus, Mycobacterium chelonae, Mycobacterium szulgai, Mycobacterium gordonae, Mycobacterium haemophilum, Mycobacterium fortuni* and *Mycobacterium marinum.*

11. The method of claim 9 wherein the the Mycobacterial infection is an infection by *Mycobacterium tuberculosis.*

12. The method of claim 10 wherein the infection by *Mycobacterium tuberculosis* is a dormant infection.

13. The method of claim 10 wherein the patient has active tuberculosis.

14. The method of claim 9 wherein $R_l$ represents a substituent bonded to carbon-4 of the pyrimidine ring, wherein said substituent is selected from the group consisting of fluorine, chlorine, bromine, iodine and trifluoromethyl.

15. The method of claim 9 wherein $R_e$ is selected from the group consisting of 5-methoxy-2-nitrophenyl, 2-nitrophenyl, 4-methylsulfonyl-2-nitrophenyl and 4-methoxyphenyl.

16. The method of claim 9 wherein $R_e$ is a substituted or unsubstituted pyrimidyl, pyrazyl, pyridyl, quinolyl, quinoxalyl or benzimidazolyl group.

17. The method of claim 16 wherein $R_e$ is 2-quinoxalyl, 4-pyrimidyl, 2-benzimidazolyl; 2-, 3- or 4-pyridyl, 2-quinolyl, 4-quinolyl and 2-pyrazyl.

18. A method of treating a bacterial infection in a patient, comprising the step of administering to the patient a therapeutically effective amount of one or more compounds of Formula III, (III)

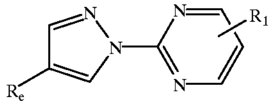

or a salt thereof with a pharmaceutically acceptable acid, wherein $R_e$ is a substituted or unsubstituted phenyl group or a substituted or unsubstituted heteroaryl group; and $R_I$ represents one or more substituents independently selected from the group consisting of hydrogen, halogen, alkyl, alkoxy, cyano, nitro and trifluoromethyl, provided that the compound is not 2-[4-(2-nitro-4-chlorophenyl)-pyrazol-1-yl]-4-trifluoromethyl pyrimidine.

19. The method of claim 18 wherein the bacterial infection is an infection by a Gram-negative bacterial species.

20. A method of treating a bacterial infection in a patient, comprising the step of administering to the patient a therapeutically effective amount of a compound represented by the following structural formula:

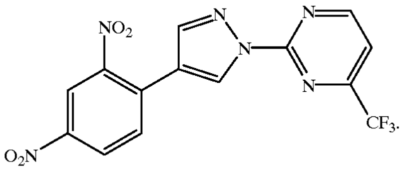

* * * * *